US008822222B2

(12) United States Patent
Beebe et al.

(10) Patent No.: US 8,822,222 B2
(45) Date of Patent: Sep. 2, 2014

(54) APPARATUS FOR GENERATING ELECTRICAL PULSES AND METHODS OF USING SAME

(75) Inventors: Stephen J. Beebe, Norfolk, VA (US); Karl H. Schoenbach, Norfolk, VA (US); Richard Heller, Norfolk, VA (US)

(73) Assignees: Eastern Virginia Medical School, Norfolk, VA (US); Old Dominion University, Norfolk, VA (US)

( * ) Notice: Subject to any disclaimer, the term of this patent is extended or adjusted under 35 U.S.C. 154(b) by 218 days.

(21) Appl. No.: 13/073,785

(22) Filed: Mar. 28, 2011

(65) Prior Publication Data

US 2011/0236979 A1    Sep. 29, 2011

Related U.S. Application Data

(62) Division of application No. 10/564,994, filed as application No. PCT/US2004/023078 on Jul. 19, 2004, now abandoned.

(60) Provisional application No. 60/487,932, filed on Jul. 18, 2003, provisional application No. 60/499,921, filed on Sep. 4, 2003, provisional application No. 60/526,585, filed on Dec. 4, 2003.

(51) Int. Cl.
*C12N 15/87* (2006.01)

(52) U.S. Cl.
USPC ........................................ 435/461; 435/173.6

(58) Field of Classification Search
None
See application file for complete search history.

(56) References Cited

U.S. PATENT DOCUMENTS

| 5,589,466 | A | 12/1996 | Felgner et al. |
| 6,326,177 | B1 | 12/2001 | Schoenbach et al. |
| 6,831,377 | B2 | 12/2004 | Yampolsky et al. |
| 2002/0010491 | A1 | 1/2002 | Schoenbach et al. |
| 2002/0140464 | A1 | 10/2002 | Yampolsky et al. |
| 2003/0170898 | A1* | 9/2003 | Gundersen et al. ........... 435/461 |
| 2011/0288545 | A1 | 11/2011 | Beebe et al. |

FOREIGN PATENT DOCUMENTS

| JP | 2003-506064 | 2/2003 |
| WO | WO-9118103 A1 | 11/1991 |
| WO | WO-0110319 A1 | 2/2001 |
| WO | WO-03047684 A2 | 6/2003 |

OTHER PUBLICATIONS

Schoenbach et al (Transactions on Plasma Science, 2002, 30:293-300).*
Beebe et al. "Diverse Effects of Nanosecond Pulsed Electric Fields on Cells and Tissues" DNA and Cell Biology, vol. 22, No. 12, pp. 785-796 (2003).
Beebe et al. "Nanosecond, High-Intensity Pulsed Electric Fields Induce Apoptosis in Human Cells" The FASEB Journal express article 10.1096/fj.02-0859fje. (2003).
Beebe, et al. "Nanosecond Pulsed Electric Field (nsPEF) Effects on Cells and Tissues: Apoptosis Induction and Tumor Growth Inhibition" IEEE Transactions on Plasma Science, vol. 30, No. 1, pp. 286-292 (2002).
Beebe, et al. "Nanosecond Pulsed Electric Fields Modulate Cell Function Through Intracellular Signal Transduction Mechanisms" Physiological Measurement, vol. 25, pp. 1077-1093 (2004).
Beebe, et al. "Nanosecond, High-Intensity Pulsed Electric Fields Induce Apoptosis in Human Cells" vol. 17, pp. 1493-1495 (2003).
Belehradek et al. "Electrochemotherapy, a New Antitumor Treatment" First Clinical Phase I-II Trial, Cancer, vol. 72, No. 12, pp. 3694-3700 (1993).
Buescher, et al. "Effects of Submicrosecond, Hight Intensity Pulsed Electric Fields on Living Cells—Intracellular Electromanipulation" vol. 10, No. 5, pp. 788-794 (2003).
Cech "Ribozymes and Their Medical Implication" JAMA, vol. 260, No. 20, pp. 3030-3034 (1988).
Chen et al. "Leukemic Cell Intracellular Responses to Nanosecond Electric Fields" Biochemical and Biophysical Research Communications, vol. 317, pp. 421-427 (2004).
Cole "Electric Impedance of Marine Egg Membranes" vol. 33, pp. 966-972 (1937).
Deng et al. "The Effects of Intense Submicrosecond Electrical Pulses on Cells" Biophysical Journal, vol. 84, pp. 2709-2714 (2003).
Dev et al. "Electrochemotherapy—A Novel Method of Cancer Treatment" Cancer Treatment Reviews, vol. 20, pp. 105-115 (1994).
Dev et al. "Medical Applications of Electroporation" IEEE Transactions on Plasma Science, vol. 28, No. 1, pp. 206-223 (2000).
Djuzenova et al. "Effect of Medium Conductivity and Composition on the Uptake of Propidium Iodide Into Electropermeabilized Myeloma Cells" Biochimica et Biophysica Acta 1284, pp. 143-152 (1996).
European Patent Application No. 04809502 Supplementary Search Report (search completed Apr. 29, 2010) (1 page).
Hasselhoff, Nature, vol. 334, No. 6183, pp. 585-591 (1988).
Helene "The Anti-Gene Strategy: Control of Gene Expression by Triplex-Forming-Oligonucleotides" Anti-Cancer Drug Design, vol. 6, pp. 569-584 (1991).

(Continued)

*Primary Examiner* — Sean Aeder
*Assistant Examiner* — Julie Wu
(74) *Attorney, Agent, or Firm* — Wilmer Cutler Pickering Hale and Dorr LLP

(57) ABSTRACT

A method and apparatus are provided for delivering an agent into a cell through the application of nanosecond pulse electric fields ("nsPEF's"). The method includes circuitry for delivery of an agent into a cell via known methods followed by the application of nanosecond pulse electric fields to said cell in order to facilitate entry of the agent into the nucleus of the cell. In a preferred embodiment, the present invention is directed to a method of enhancing gene expression in a cell comprising the application of nanosecond pulse electric fields to said cell. An apparatus for generating long and short pulses according to the present invention is also provided. The apparatus includes a pulse generator capable of producing a first pulse having a long duration and low voltage amplitude and a second pulse having a short duration and high voltage amplitude.

18 Claims, 7 Drawing Sheets

(56) References Cited

OTHER PUBLICATIONS

Heller et al. "Phase I/II Trial for the Treatment of Cutaneous and Subcutaneous Tumors Using Electrochemotherapy" Cancer, vol. 77, No. 964-971 (1996).

Hofmann et al. "Electric Field Pulses Can Induce Apoptosis" J. Membrane Biol., vol. 169, pp. 103-109 (1999).

Hofmann et al. "Electroporation Therapy: A New Approach for the Treatment of Head and Neck Cancer" IEEE Transactions on Biomedical Engineering, vol. 46, No. 6, pp. 752-759 (1999).

Maher et al. "Oligonucleotide-Directed DNA Triple-Helix Formation: An Approach to Artificial Repressors?" Antisense Research and Development, vol. 1, pp. 277-281 (1991).

Mankowski et al. "A Review of Short Pulse Generator Technology" IEEE Transactions of Plasma Science, vol. 28, No. 1, pp. 102-108 (2000).

Mir et al. "Mechanisms of Electrochemotherapy" Advanced Drug Delivery Reviews 35, pp. 107-118 (1999).

Neumann et al. "Fundamentals of Electroporative Delivery of Drugs and Genes" Bioelectrochemistry and Bioenergetics, vol. 48, pp. 3-16 (1999).

PCT Search Report for International Application No. PCT/US2004/023078 dated Nov. 30, 2005 (5 pages).

Schoenbach et al. "Bioelectrics—New Applications for Pulsed Power Technology" IEEE Transactions on Plasma Science, vol. 30, No. 1, pp. 293-300 (2002).

Schoenbach et al. "Biological/Medical Pulsed Electric field Treatments" pp. 42-46 (2000).

Schoenbach et al. "Intracellular Effect of Ultrashort Electrical Pulses" Bioelectromagnetics, vol. 22, pp. 440-448 (2001).

Schoenbach, et al. "Bacterial Decontamination of Liquids with Pulsed Electric Fields" vol. 7, No. 5, pp. 637-645 (2000).

Schoenbach, et al. "The Effect of Pulsed Electric Fields on Biological Cells: Experiments and Applications" vol. 25, No. 2, pp. 284-292 (1997).

Schoenbach, et al. "Ultrashort Electrical Pulses Open a New Gateway Into Biological Cells" Proceedings of the IEEE, vol. 92, No. 7, pp. 1122-1137 (2004).

Vernier et al. "Calcium Bursts Induced by Nanosecond Electric Pulses" Biochemical and Biophysical Research Communications, vol. 310, pp. 286-295 (2003).

Weaver "Electroporation of Cells and Tissues" pp. 1431-1440 (1995).

Weaver et al. "Theory of Electrical Creation of Aqueous Pathways Across Skin Transport Barriers" Advanced Drug Delivery Reviews, vol. 35, pp. 21-39 (1999).

White et al. "Stimulation fo Capacitative Calcium Entry in HL-60 Cells by Nanosecond Pulsed Electric Fields" The Journal of Biological Chemistry, vol. 279, No. 22, pp. 22964-22972 (2004).

Zimmermann et al. "Electromanipulation of Mammalian Cells: Fundamentals and Application" vol. 28, No. 1, pp. 72-82 (2000).

Schoenbach et al, "Bioelectrics—New Applications for Pulsed Power Technology" IEEE Transactions on Plasma Science, vol. 30, No. 1, Feb. 2002, pp. 293-300.

Hudson Alpha/Caltech ENCODE Group, "Cell Growth Protocol for Jurkat Cell Line", Aug. 27, 2008, 2 pages.

Panje et al, "Electroporation Therapy of Head and Neck Cancer", Annual Otology, Rhinology, Laryngology, vol. 107 (9 Pt. 1), Sep. 1998 (Abstract).

* cited by examiner

APPARATUS FOR GENERATING ELECTRICAL PULSES AND METHODS OF USING SAME

REFERENCE TO RELATED APPLICATIONS

This application is a divisional of co-pending U.S. patent application Ser. No. 10/564,994, filed Jul. 24, 2006, which is a 371 application of PCT/US2004/023078, filed Jul. 19, 2004, which claims the benefit of U.S. Provisional Application No. 60/487,932, filed Jul. 18, 2003, U.S. Provisional Application No. 60/499,921, filed Sep. 4, 2003, and U.S. Provisional Application No. 60/526,585, filed Dec. 4, 2003, the disclosures of which are incorporated herein by reference.

STATEMENT AS TO RIGHTS TO INVENTIONS MADE UNDER FEDERALLY SPONSORED RESEARCH AND DEVELOPMENT

The present invention was made with Government support under AFOSR MURI Grant No. F49620-02-1-0320 awarded by the United States Air Force Office of Scientific Research. The Government has certain rights in the invention.

BACKGROUND OF THE INVENTION

Both the detection and use of electricity/electric fields in medicine and biology are widespread and well accepted. Electrocardiography (EKG) and electroencephalography (EEG) are used to detect electrical activity in the heart and brain, respectively. Cardioversion, the application of a pulsed electric field to heart muscle, is routinely used to stop, modify, or re-start the heart's beating. Low power electric fields can be applied to bone fractures to stimulate healing. Electromyography, the application of measured electrical pulses to muscles or their associated nerves, can be used to measure muscle function and/or judge the degrees of muscle damage. In biology, electric fields have various applications and can be used, for example, to separate molecules of different sizes (electrophoresis) or different charges (isoelectric focusing), and to separate cells with different characteristics (cell sorting during flow cytometry). Electric fields can also be used to facilitate entry of new proteins or genes into living cells via a process called electroporation.

In electroporation, application of brief (on the scale of thousandths-to-millionths of a second), moderate power (kilovolt/meter) electric fields causes permeabilization (leakiness) of the cell's surface membrane which then allows entry of materials/molecules into the cell that would otherwise never gain access to the cell's interior. After the initial permeabilization of the cell membrane, the cell eventually returns to its normal "non-leaky" condition. Now, however, the cell will carry and/or utilize the materials that have been introduced into it by the electroporation. This process can be used for the introduction of genes or drugs into a cell, for example, for transdermal drug delivery (Neumann, E., Kakorin, S., and Toensing, K. (1999), Fundamentals of electroporative delivery of drugs and genes. Bioelectrochem. Bioenerg. 48, 3-16.1999; Weaver, J. C., Vaughan, T. E., and Chizmadzhev, Y. (1999), Theory of electrical creation of aqueous pathways across skin transport barriers. Adv. Drug Deliv. Rev. 35, 21-39), and as a therapeutic tool for the treatment of cancer using electrochemotherepy (Belehradek, M., Domenge, C., Luboinski, B., Orlowski, S., Belehradek, J. Jr., and Mir, L. M. (1993), Electrochemotherapy, a new antitumor treatment. First clinical phase I-II trial. Cancer 72, 3694-700.1993; Heller, R., Jaroszeski, M. J., Glass, L. F., Messina, J. L., Rapaport, D. P., DeConti, R. C., Fenske, N. A., Gilbert, R. A., Mir, L. M., Reintgen, D. S. (1996), Phase I/II trial for the treatment of cutaneous and subcutaneous tumors using electrochemotherapy. Cancer 77, 964-71.1996; Hofmann, F., Ohnimus, H., Scheller, C., Strupp, W., Zimmermann, U., and Jassoy, C. (1999), Electric field pulses can induce apoptosis. J. Membr. Biol. 169, 103-109). Electrochemotherapy or electroporation therapy (EPT) is a method for the in vivo delivery of poorly permeable chemotherapeutic agents, such as bleomycin, to tumor cells that can be appropriately oriented between two electrodes (Dev S. B., Hofmann, G. A., Electrochemotherapy—a novel method of cancer treatment. Cancer Treat Rev 20:105-15, 1994; Hofmann et al., Electroporation therapy: a new approach for the treatment of head and neck cancer. IEE Trans Biomed Eng 46:752-9, 1999; Mir, L. M., Orlowski, S. Mechanisms of electrochemotherapy. Adv Drug Deliv Rev., 35:107-118, 1999). Both electroporation and EPT are dependent on electric effects on the plasma membrane of the cells or tissues.

Electroporation occurs with pulse durations on the order of 0.1 to 20 milliseconds ("ms") (Dev, S. B., Rabussay, D. A., Widera, G., and Hofmann, G. A. (2000) *IEEE Trans. Plasma Sci.* 28, 206-223) with electric fields on the order of volts to low kilovolts/centimeter; however, specific conditions depend on the particular cell type and the cell suspension media. These millisecond pulses promote transient membrane poration and cell survival. Alternatively, using different electrical or cellular conditions, electroporation can cause rupture/death of cells. Although the physical nature of the pores is not well characterized, the experimental conditions that allow intracellular delivery of membrane impermeable molecules with good cell survivability are well known. Conditions for optimal electroporation depend on the waveform, the constituents of the media in which the cell is suspended, and the cell type (Weaver, J. C., Electroporation of cells and tissues, in: J. D. Bronzino (Ed.), The Biomedical Engineering Handbook, CRC and IEEE press, Boca Raton, Fla., 1995, pp. 1431-1440; Djuzenova et al., Effect of medium conductivity and composition on the uptake of propidium iodide into electropermeabilized myeloma cells. Biochim Biophys Acta, 1284:143-52, 1996). In any case, the electroporation effects of these millisecond low power applied electric fields occur only at the cell's surface membrane.

As mentioned above, electric fields and the process of electroporation have also been used for the introduction of genes into cells. The transfection of living cells with DNA is a common molecular technique used to express exogenous genes in cells for transcription studies or for therapeutic purposes in the treatment of some diseases. Known transfection methods include the incorporation of DNA into lipid vesicles for fusion with the plasma membrane, the endocytosis of DNA precipitated with calcium phosphate or dextran, the use of viral vectors that infect the cell with the gene of interest, and electropermeabilization or electroporation using pulsed electric fields that form "pores" in the plasma membrane. Some cell types, especially those that grow in suspension, can only be effectively transfected by electropermeabilization. Enhanced or optimized gene expression has been previously accomplished using classical electroporation pulses by changing the pulse duration of a long pulsed electric field (for example, within the range of 1 microsecond-20 milliseconds), changing the electric field intensity within classical electroporation range (0.1-5 kV/cm), and/or by modifying the conductivity of the buffer or media. In other transfection procedures enhanced gene expression has been accomplished by changing the concentration of DNA used in the transfection procedure, changing the physical/chemical properties during transfection (pH, ionic strength, etc), using various lipid combinations with different properties, or adding other constituents to the cell culture media or buffers to aid transfection efficiency.

Even with these known techniques, more efficient methods of introducing an agent into a cell and new methods of enhancing gene expression are still needed. These and various other needs are addressed, at least in part, by one or more embodiments of the present invention.

SUMMARY OF THE INVENTION

The present invention is directed to a method of introducing an agent into a cell comprising the application of nanosecond pulse electric fields ("nsPEF's").

In accordance with one or more embodiments of the invention, a method for introducing an agent into a cell includes providing a preparation comprising the cell and agent, and applying the nanosecond pulse electric fields to said preparation, which facilitates the entry of the agent into the nucleus. The nsPEFs can range in time from 1 to 1000 nanoseconds, preferably 1 to 300 nanoseconds. The nsPEFs can also range in electric field intensity from 1 to 1000 kV/cm, preferably 10 to 350 kV/cm. The agent may be selected from the group comprising drugs, nucleic acids, protein, peptides, and polypeptides, for example.

Various embodiments of the invention allow the drug to be an antibiotic or a chemotherapeutic agent selected from the group comprising bleomycin, daunomycin, 5-FU, cytosine arabinoside, colchicine, cytochalasin B, daunorubicin, neocarcinostatin, suramin, doxorubicin, carboplatin, taxol, mitomycin C, vincristine, vinblastine, methotrexate, and cisplatin, and suitable combinations thereof. Furthermore, the agent can be a nucleic acid, wherein the nucleic acid is selected from the group comprising DNA, cDNA, and RNA. According to the present invention, these nucleic acids may encode a homologous or heterologous gene product and the cell can be transfected so that this gene product is expressed in the cell. The nucleic acid can also be an expression vector wherein the expression vector contains a homologous or heterologous nucleic acid encoding a gene product operably linked to a suitable promoter sequence. The nucleic acid may also modify the expression of a gene and provide gene therapy, for example. The nucleic acid introduced into the cell may also modulate cell proliferation or elicit an immune response. Further embodiments of the invention provide for agents that can be in the form a polypeptide, wherein the polypeptide is selected from the group comprising a hormone, a cytokine, a lymphokine, a growth factor, or a combination thereof. The polypeptide can also be antigen or an antibody.

In accordance with additional embodiments of the invention, the agent can be a cytotoxic agent selected from the group comprising ricin, abrin, diphtheria toxin, and saporin. Any type of cell may be used in the present invention including eukaryotic cells, prokaryotic cells, fat cells, bone cells, vascular cells, muscle cells, cartilage cells, stem cells, hematopoeitic cells, lung cells, airway cells, liver cells, intestinal cells, skin cells, nerve cells, cancer cells, bacterial cells, and combinations thereof.

In accordance with at least one embodiment of the invention, a method of enhancing gene expression includes providing a preparation comprising the cell and the nucleotide sequence to be delivered into the cell, and applying nanosecond pulse electric fields to said preparation, wherein said application facilitates the entry of the agent into the nucleus.

In other forms of the invention, a method of enhancing gene expression in a cell includes transfecting a cell with a desired gene and applying nanosecond pulse electric fields to a cell. The cell may be transfected by any commonly known method, including but not limited to, electroporation, the use of lipid vesicles, the use of viral vectors, and/or co-precipitation with calcium phosphate or dextran.

In various embodiments of the invention, a method of enhancing gene expression in a cell includes applying one or more long pulses to a cell and applying one or more nanosecond pulse electric field pulses to said cell. These long pulses can range in duration from about 0.001 to 30 milliseconds, preferably about 0.1 to 20 milliseconds, and can have electric field intensities ranging from about 0.1 to 5 kV/cm, preferably 0.1 to 1 kV/cm. The nsPEFs can range in time from 1 to 1000 nanoseconds, preferably 1 to 300 nanoseconds. The nsPEFs can also range in electric field intensity from 1 to 1000 kV/cm, preferably 10 to 350 kV/cm.

In another embodiment, a method of enhancing delivery of drugs to tumors or other tissues includes applying nanosecond pulse electric fields to said tumors or other tissues. The nsPEFs can range in time from 1 to 1000 nanoseconds, preferably 1 to 300 nanoseconds. The nsPEFs can also range in electric field intensity from 1 to 1000 kV/cm, preferably 10 to 350 kV/cm.

In another embodiment, a method of delivering a vaccine to a cell includes applying nanosecond pulse electric fields to a cell. The nsPEFs can range in time from 1 to 1000 nanoseconds, preferably 1 to 300 nanoseconds. The nsPEFs can also range in electric field intensity from 1 to 1000 kV/cm, preferably 10 to 350 kV/cm.

In another embodiment, a method of applying nanosecond pulse electric fields is provided in which the nsPEFs are applied to a patient in need of therapy thereof. The nsPEFs can range in time from 1 to 1000 nanoseconds, preferably 1 to 300 nanoseconds. The nsPEFs can also range in electric field intensity from 1 to 1000 kV/cm, preferably 10 to 350 kV/cm. The patient in need may, for example, have cancer.

In another embodiment, a method of enhancing gene expression in a cell comprising applying a nanosecond pulse electric field to said cell is provided. The nsPEFs can range in time from 1 to 1000 nanoseconds, preferably 1 to 300 nanoseconds. The nsPEFs can also range in electric field intensity from 1 to 1000 kV/cm, preferably 10 to 350 kV/cm.

In accordance with one or more embodiments of the invention, a pulse generator is provided for generating electrical pulses. The pulse generator includes a first circuit, a second circuit, and a control circuit. The first circuit is used to generate a first pulse having a long duration and low voltage amplitude. The second circuit is used to generate a second pulse having a short duration and high voltage amplitude. The control circuit is provided for controlling the timing of the first and second circuits such that the first and second pulses are respectively generated.

Various embodiments of the invention allow the length of the first pulse to range from 0.001 to 30 milliseconds. The electric field of the first pulse can also range from 0.1 kV/cm to 5 kV/cm. The length of the second pulse can vary from 1 to 1000 nanoseconds, while the electric field strength can range from 1 kV/cm to 1000 kV/cm. Furthermore, the control circuit can vary the interval between the first and second pulses.

Other embodiments of the invention provide for a first circuit that includes a high voltage power supply and a charging resistor coupled to the high voltage power supply. A capacitor is coupled to the charging resistor at a first end and coupled to a load at a second end. A transistor is provided for controlling electrical discharge of the capacitor to the load. The second circuit can be configured such that it includes a high voltage power supply, a charging resistor coupled to the high voltage power supply; and a transmission line coupled at a first end to the charging resistor and coupled at a second end to a load. The transmission line functions to discharge electricity into the load.

In accordance with at least one embodiment of the invention, a method is provided for enhancing gene expression using a pulse generator. The method comprises the steps: triggering a first pulse having a long duration and low voltage amplitude from a first circuit of the pulse generator; delivering the first pulse to at least one cell to cause electroporation at the plasma membrane of the at least one cell; triggering a second pulse having a long duration and low voltage amplitude from a second circuit of the pulse generator; and delivering the second pulse to the at least one cell to cause electroporation at the nuclear membrane of the at least one cell.

In accordance with one or more embodiments of the invention, a method is provided for enhancing gene expression in a cell using a multi-pulse generator. The method comprises the steps: charging a capacitor; triggering a high voltage, high current transistor to initiate discharge of the charge accumulated in the capacitor into at least one cell to cause electroporation at the plasma membrane of the at least one cell; triggering the high voltage, high current transistor to stop the discharge of the capacitor after a predetermined long duration; actuating a switch to decouple the capacitor from the at least one cell; charging a transmission line; triggering a high voltage switch to initiate discharge of the charge accumulated in the transmission line into the at lest one cell to cause electroporation at the nuclear membrane of the at least one cell; and triggering the high voltage switch to stop discharge of the transmission line after a predetermined short duration.

Other embodiments of the present invention provide for a dual-pulse generator for enhancing gene expression in a cell. The dual-pulse generator comprises a first pulse generator, a second pulse generator, and a control circuit. The first pulse generator is used to generate a first pulse having a long duration and low voltage amplitude. The second pulse generator is used to generate a second pulse having a short duration and high voltage amplitude. The first pulse causes electroporation of the cellular plasma membrane of the cell, while second pulse causes electroporation of the nuclear membrane of the cell. The control circuit is used to control the timing of the pulses generated by the first and second pulse generators.

It is to be understood that the invention is not limited in its application to the details of construction and to the arrangements of the components set forth in the following description or illustrated in the drawings. Rather, the invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These, and various features of novelty which characterize the invention, are pointed out with particularity in the appended claims forming a part of this disclosure. For a better understanding of the invention, its operating advantages and the specific benefits attained by its uses, reference should be had to the accompanying drawings and preferred embodiments of the invention illustrating the best mode contemplated for practicing the invention.

DETAILED DESCRIPTION OF THE INVENTION

Figure 1:
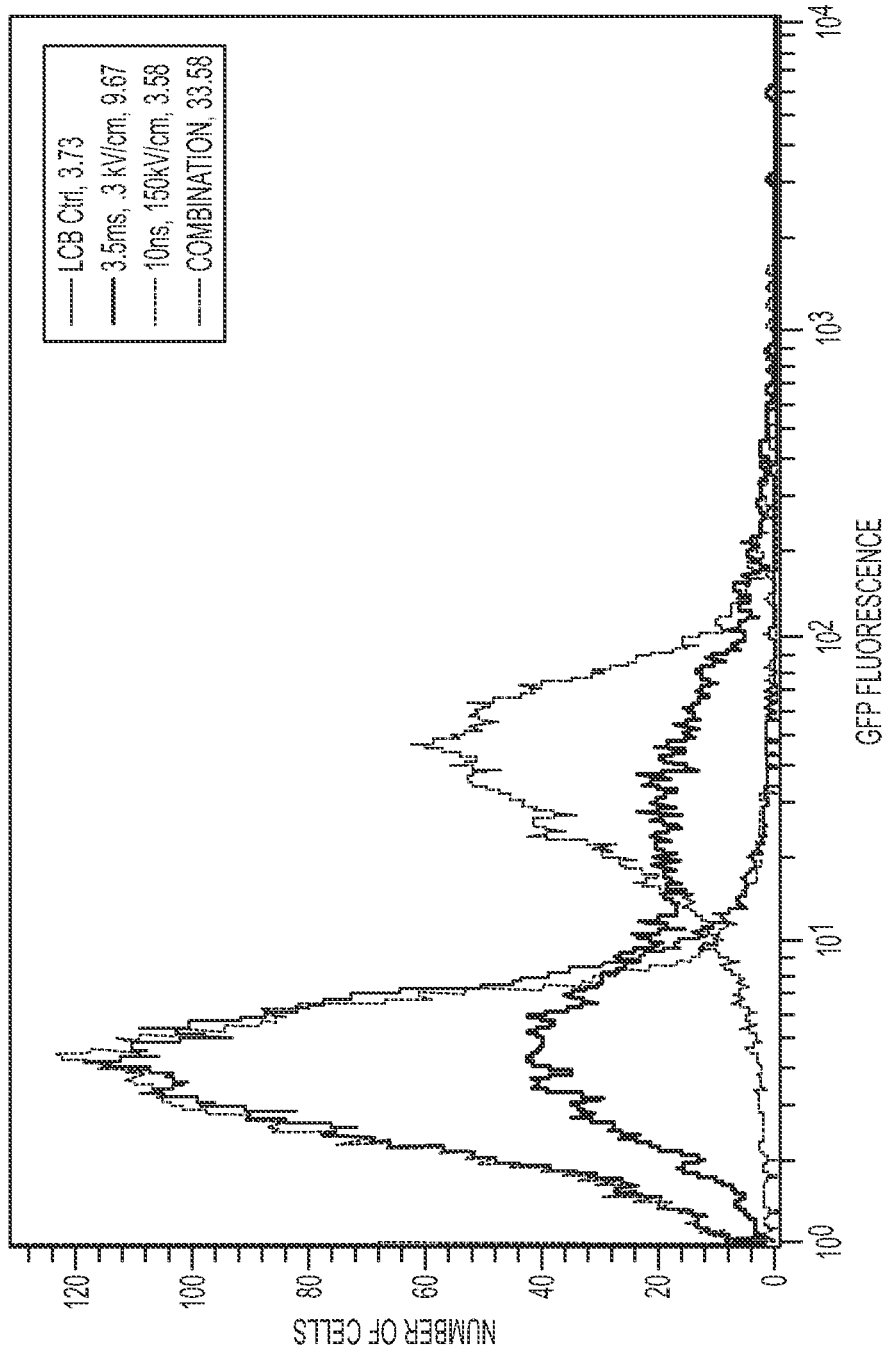
FIG. 1 shows a typical experiment with HL-60 cells that were exposed, in the presence of a Green Fluorescent Protein ("GFP") reporter gene driven by a constitutive cytomegalovirus ("CMV") promoter, to a classical plasma membrane electroporation (long) pulse, a short nsPEF pulse, a combination of a long pulse followed thirty minutes later by a short nsPEF pulse, or no pulse. The cells shown in FIG. 1 were exposed to a long pulse of 3.5 milliseconds ("ms") and 0.3 kV/cm, a short nsPEF pulse of 10 nanoseconds ("ns") and 150 kV/cm, or a combination of the long and short pulse. GFP fluorescence is depicted on the x-axis while the number of cells fluorescing is depicted on the y-axis. The observed geometric mean GFP fluorescence is listed next to each pulsing condition.
Figure 2:
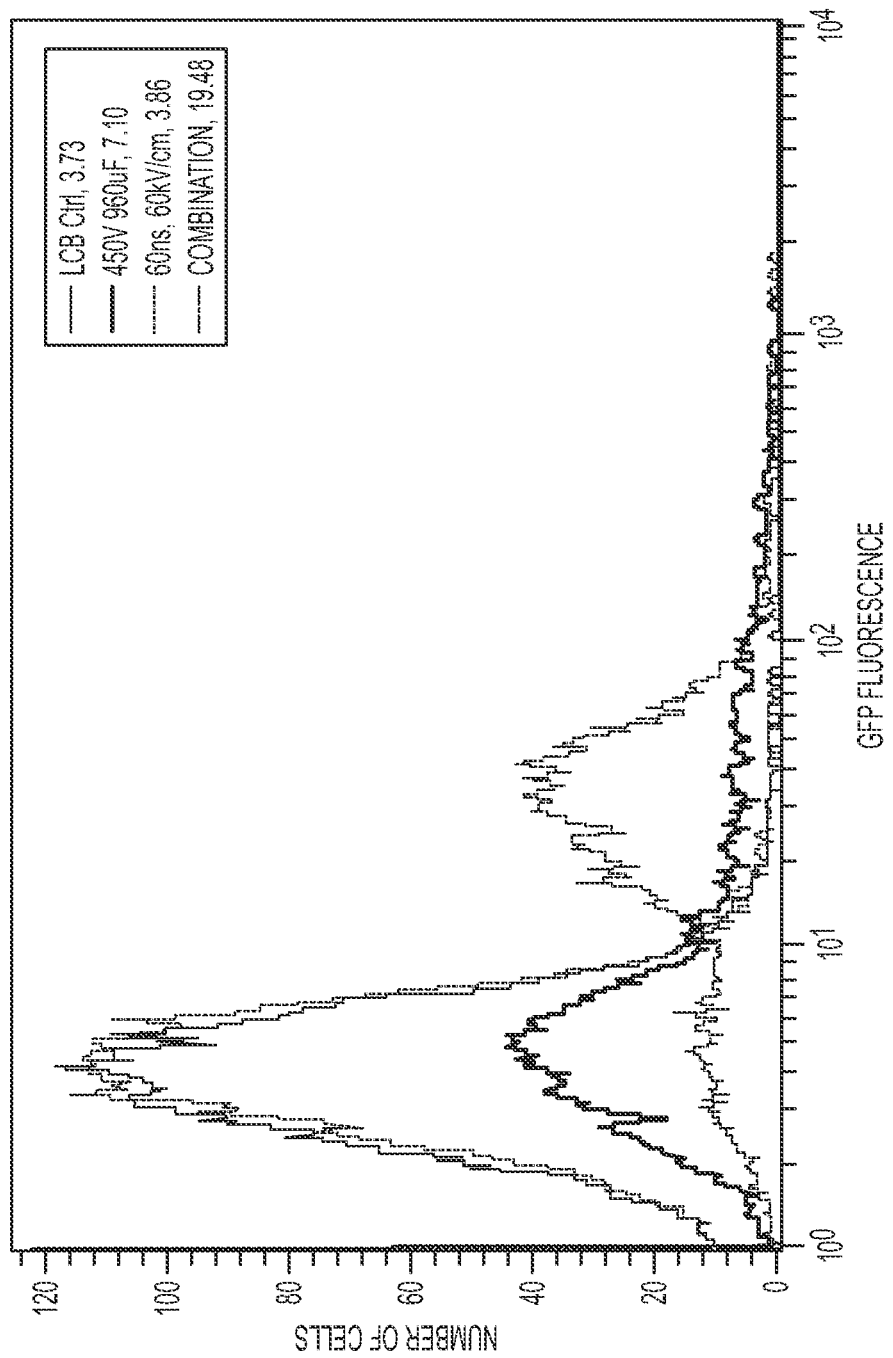
FIG. 2 shows a similar experiment in which HL-60 cells were exposed to a long pulse of 450 V and 960 uF, a short nsPEF pulse of 60 ns and 60 kV/cm, or a combination of the long and short pulse. The observed geometric mean GFP fluorescence is listed next to the pulsing conditions in the inset of the figure.
Figure 3:
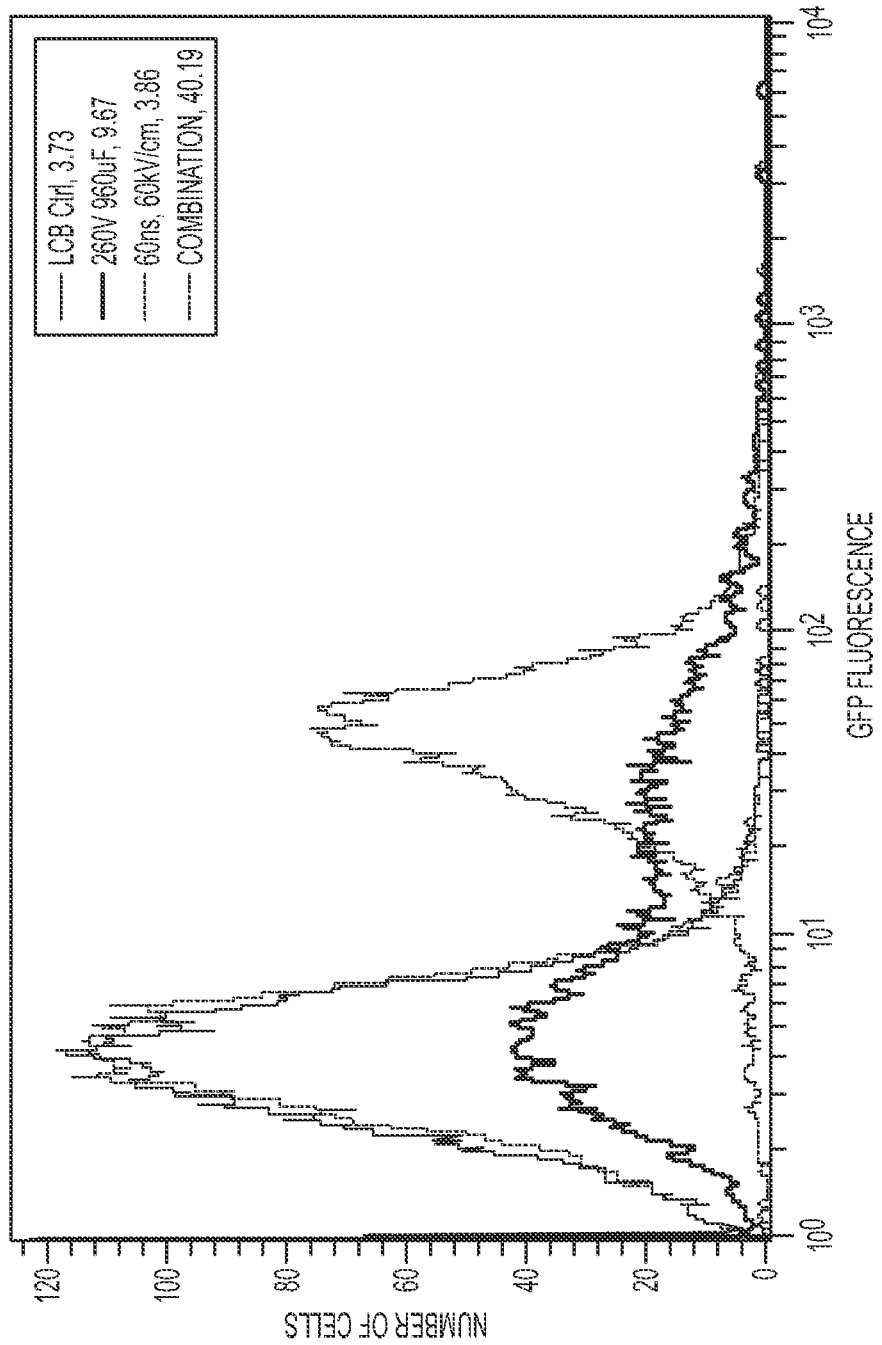
FIG. 3 shows a similar experiment in which HL-60 cells were exposed to a long pulse of 260 V and 960 uF, a short nsPEF pulse of 60 ns and 60 kV/cm, or a combination of the long and short pulse. The observed geometric mean GFP fluorescence is listed next to the pulsing conditions in the inset of the figure.
Figure 4:
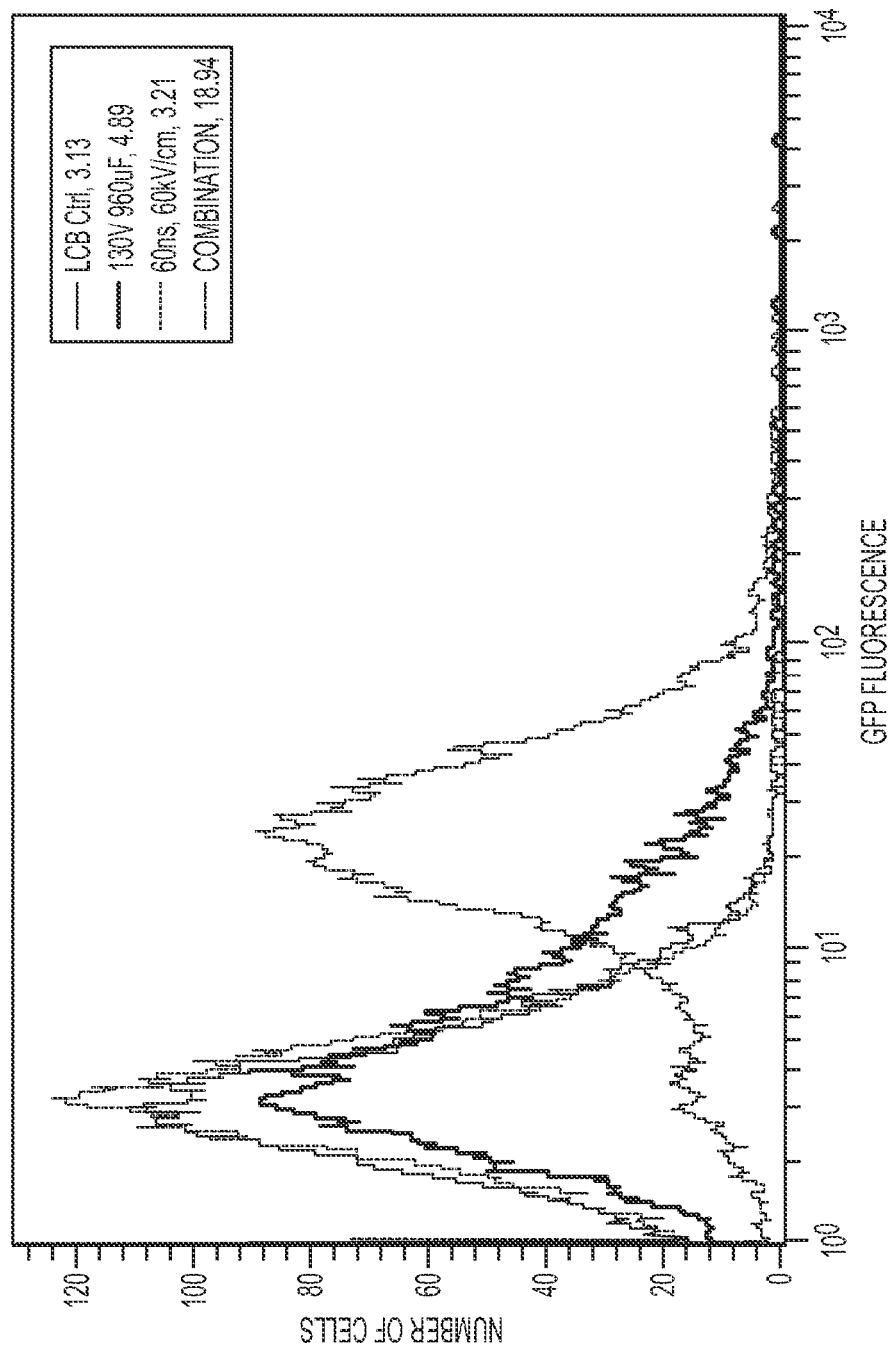
FIG. 4 shows a similar experiment in which HL-60 cells were exposed to a long pulse of 130 V and 960 uF, a short nsPEF pulse of 60 ns and 60 kV/cm, or a combination of the long and short pulse. The observed geometric mean GFP fluorescence is listed next to the pulsing conditions in the inset of the figure.
Figure 5:
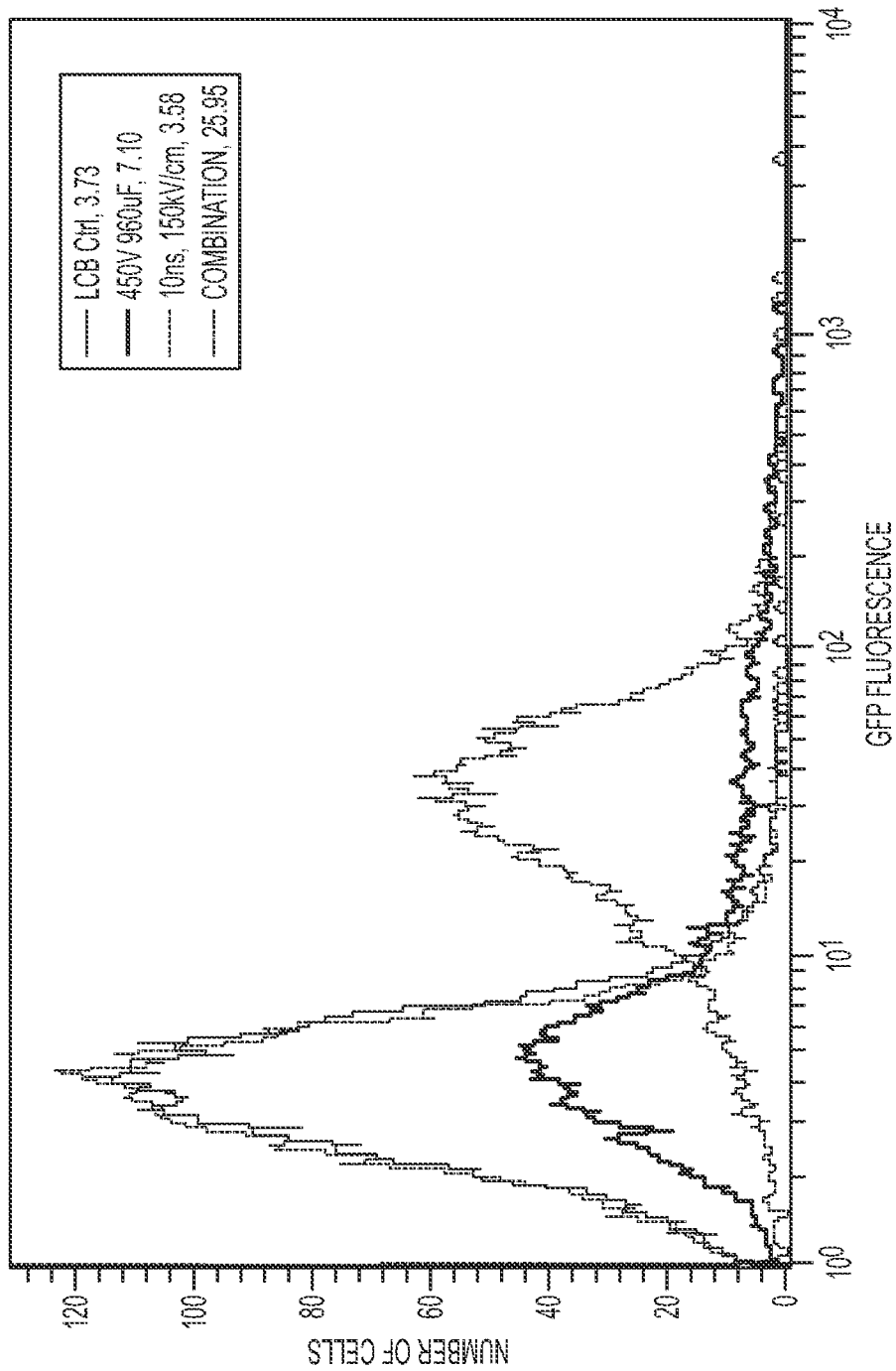
FIG. 5 shows a similar experiment in which HL-60 cells were exposed to a long pulse of 450 V and 960 uF, a short nsPEF pulse of 10 ns and 150 kV/cm, or a combination of the long and short pulse. The observed geometric mean GFP fluorescence is listed next to the pulsing conditions in the inset of the figure.
Figure 6:
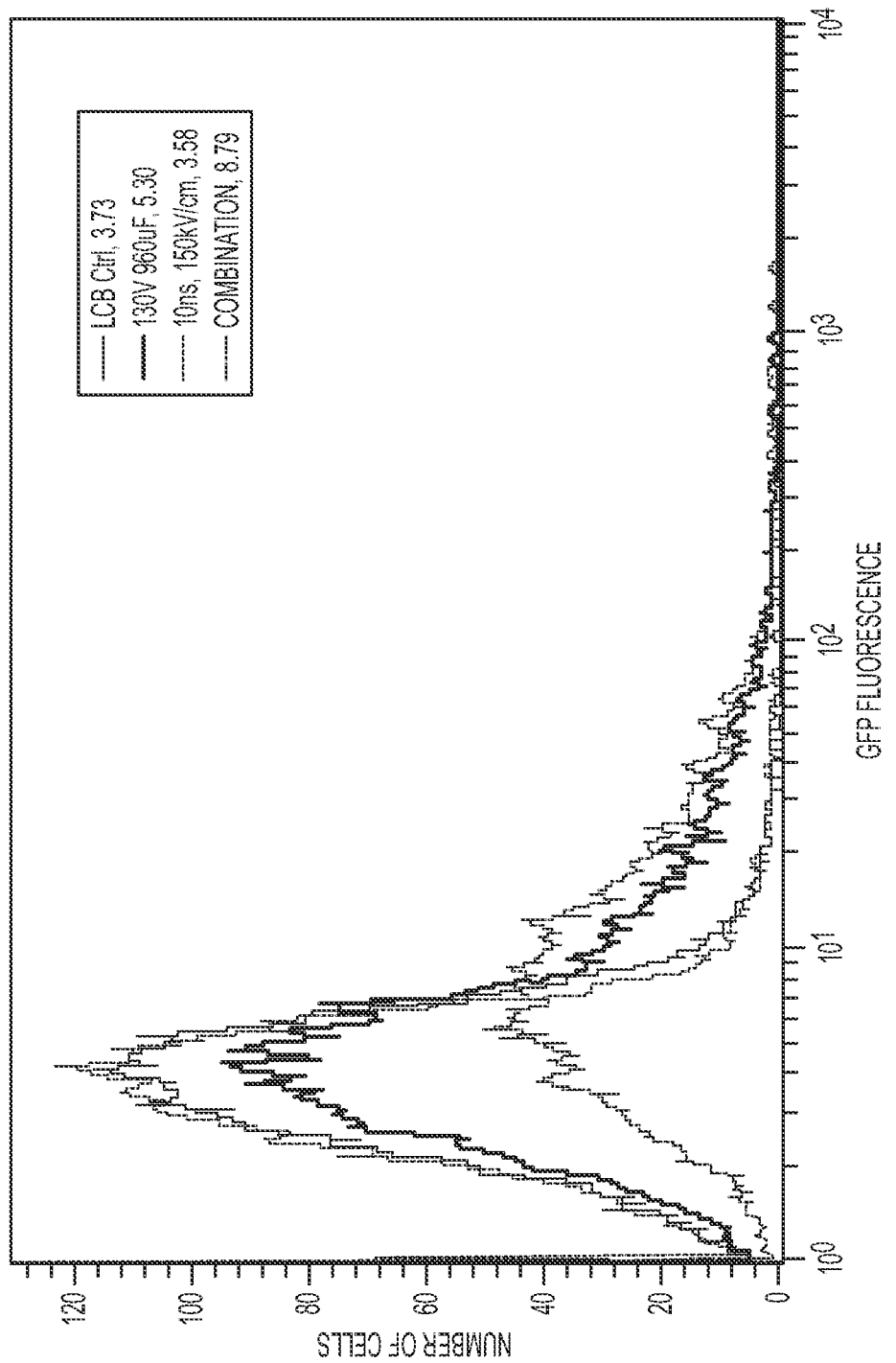
FIG. 6 shows a similar experiment in which HL-60 cells were exposed to a long pulse of 130 V and 960 uF, a short nsPEF pulse of 10 ns and 150 kV/cm, or a combination of the long and short pulse. The observed geometric mean GFP fluorescence is listed next to the pulsing conditions in the inset of the figure.

For the purposes of promoting an understanding of the principles of the invention, reference will now be made to preferred embodiments and specific language will be used to describe the same. It will nevertheless be understood that no limitation of the scope of the invention is thereby intended. Alterations and further modifications of the invention, and such further applications of the principles of the invention as illustrated herein, as would normally occur to one skilled in the art to which the invention relates are further contemplated herein.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

One aspect of the present invention is directed to a method for introducing an agent into a cell comprising the application of nanosecond pulse electric fields ("nsPEF's") to said cell. As used herein, the term "agent" includes drugs (e.g., chemotherapeutic agents), nucleic acids (e.g., polynucleotides, genes), peptides and polypeptides (including antibodies), and other molecules for delivery into a cell. "nsPEF's" as used herein are defined as electric pulses in the nanosecond ("ns") range from 1 to 1000 ns, preferably 1 to 300 ns, with high electric field intensities from I to 1000 kV/cm, preferably 10 to 350 kV/cm. The nsPEF conditions defined herein are distinctly different than electroporation pulses, not only in their temporal and electrical characteristics, but especially in their effects on intact cells and tissues. For comparative purposes, classical electroporation utilizes pulses in the microsecond to millisecond range with different pulse shapes (trapezoidal, exponential decaying) and electric fields with strengths of about 0.1 to 5 kV/cm. The rise times of classical electroporation pulses are generally longer than the charging time of the cell membrane and, therefore, will not allow an electric field to reach into the cell. By contrast, nsPEF pulses are almost rectangular pulses in the nanosecond range, preferably 10 to 300 ns, with rapid rise times, short compared to the charging time of the outer cell membrane and ranging from 1 to 30 ns, and high electric fields ranging from about 1 to 1000 kV/cm, preferably about 10 to 350 kV/cm. Except for the fast rise and fall times of the pulses, the field strength during the pulse remains at a nearly constant level. In the frequency domain, nsPEFs can be described as wideband radiation with a cut-off frequency defined by the inverse of the pulse length, ranging from 1 MHz for a pulse of 1000 ns duration to 1 GHz for a 1 ns pulse. But even for lower cut-off frequencies, the spectra show contributions of higher harmonics, primarily determined by the pulse rise time, up into the GHz range. Furthermore, classical electroporation pulses exhibit energy densities in the joules/cc range and power of about 500 W. By contrast, nsPEF pulses exhibit energy densities in the millijoules/cc range, with total energies not exceeding 10 J (preferably less than 1 J) and power of about 180 MW. About 90% of the energy contained in a nsPEF pulse is applied in a frequency range up to 60% of the cut-off frequency. In addition to the unique short duration and rapid rise time, nsPEFs are exceptional because they are very low energy and extremely high power. Thus, nsPEF pulses can be five to six orders of magnitude shorter, with electric fields and power several orders of magnitude higher, and energy densities considerably lower than electroporation pulses. Even though nsPEF pulses exhibit extremely high power, because their duration is so short, the energy density does not cause significant thermal effects.

Furthermore, nsPEF pulses and classic electroporation pulses have dramatically different effects on cells. In order to understand these differences, it is necessary to understand the basic effects of an electric field on a cell. The cell cytoplasm is a conductive body and the surrounding plasma membrane is a dielectric layer. When cells are placed in a conductive medium between 2 electrodes and a unipolar voltage pulse is applied to the electrodes, the resulting current causes accumulation of electrical charges at the cell membrane and, consequently, a voltage across the membrane. If the membrane voltage exceeds a critical value, structural changes in the surface membrane occur with trans-membrane pore formation, a process known as electroporation (Weaver, J. C., Electroporation of cells and tissues, in: J. D. Bronzino (Ed.), The Biomedical Engineering Handbook, CRC and IEEE press, Boca Raton, Fla., 1995, pp. 1431-1440). If the membrane voltage is not excessive and the duration of the pulse is limited, membrane poration can be reversible and the cell survives. The time required to charge the surface membrane is dependent upon parameters such as the cell diameter (D), resistivities of the cytoplasm (p) and suspension medium ($\rho_c$), and capacitance of the surface membrane per unit area (eR). For a spherical cell with a surface membrane that is an ideal dielectric (no leakage currents), with a diameter of 10 μm, resistivities of cytoplasm and medium of 100 ohm/cm, and a membrane capacitance of 1 μFarad/cm$^2$, the charging time constant ($\tau_c$) would be 75 ns (Cole, K. S. Electric Impedance of Marine Egg Membranes. Trans Farady Soc 23:966, 1937) [$\tau_c(\rho_c+\rho_d/2)$cmD/2]. The charging time constant is a measure of the time during which the cell interior is exposed to the applied pulsed electric field intensity. A simple electrical model for living cells predicts that when the electric pulse duration is reduced into the sub-microsecond range (time domain) there is an increasing probability that electric field interactions will occur at the level of cell substructures and a decreasing probability that the plasma membrane will be modified. Stated another way, the outer membrane becomes increasingly transparent for oscillating electric fields when the angular frequency of the oscillation exceeds a value given by the inverse of the charging time. Therefore, the use of high frequencies and short durations in the form of nsPEF pulses is more likely to achieve intracellular effects such as the electroporation of intracellular membranes.

Hence, as the pulse duration decreases, nsPEF pulses bypass the plasma membrane and target intracellular structures such as the mitochondria and nucleus, leaving the plasma membrane intact. Therefore, nsPEF pulses have effects that are different than those of electroporation pulses because, when the pulse duration is short enough and the electric field intensity is high enough, intracellular structures are targeted. (Deng et al., Biophys. J. 84, 2709-2714 (2003); Beebe et al., IEEE Trans. Plasma Sci. 30:1 Part 2, 286-292 (2002); Beebe et al., FASEB J (2003); Vernier et al., Biochem. Biophys. Res. Comm. 310, 286-295 (2003); White et. al., J Biol. Chem. 279(22):22964-72 (2004); Chen et al., Biochem Biophys Res Commun 317(2):421-7 (2004)). The effects of nsPEF's on cells differ depending on such factors as cell type, pulse duration and rise-time, electric field intensity, and the number of pulses.

In one form of the invention, a desired agent is introduced into a cell using a known technique (i.e., electroporation, lipid vesicles, viral vectors, co-precipitation with calcium phosphate or dextran). The cell is then exposed to one or more nsPEF pulses in order to facilitate transfer of the desired agent into the nucleus of the cell. According to the present invention, the nsPEF pulse can range in duration from 1 to 1000 nanoseconds, preferably 1 to 300 nanoseconds. The field amplitude for the nsPEF pulse can range from 1 to 1000 kV/cm, preferably 10 to 350 kV/cm. Experiments on the effects of nsPEFs on the plasma membrane have demonstrated that nsPEfs cause pores in the plasma membrane to open transiently, without permanently damaging the cell. (Schoenbach, K. H., Beebe, S. J., Buescher, E. S., Intracellular effect of ultrashort electrical pulses, Bioelectromagnetics 22:440-448, 2001). Other experiments with nsPEFs have shown that membrane bound organelles in the cell can be opened by the same kind of pulses. (Schoenbach, K. H., Beebe, S. J., Buescher, E. S., Intracellular effect of ultrashort electrical pulses, Bioelectromagnetics 22:440-448, 2001). Theoretically, nsPEFs are significantly short enough that the plasma membrane of a cell pulsed with these nsPEFs is not fully charged, thereby avoiding significant plasma membrane effects (unlike classical electroporation pulses). Instead, application of nsPEF to a cell results in greater effects on intracellular membranes. Although not intending to be bound by a particular theory, it is, therefore, hypothesized that nsPEFs temporarily open the nuclear membrane pores without damaging the cell. Therefore, if nsPEF pulses are applied after the desired agent has already passed through the plasma membrane of a cell, and the agent is allowed sufficient time to diffuse into the nucleus, nsPEF pulses facilitate an increased flux of the agent into the nucleus by opening up pores in the nuclear membrane.

As described earlier, the term "agent" as used herein refers to drugs (e.g., chemotherapeutic agents), nucleic acids (e.g., polynucleotides), and peptides and polypeptides (including antibodies). For example, the peptide or polypeptide used in the method of the present invention can be an antigen introduced for the purpose of raising an immune response in the subject into whose cells it is introduced. Alternatively, the polypeptide can be a hormone such as calcitonin, parathyroid hormone, erythropoietin, insulin, a cytokine, a lymphokine, a growth hormone, a growth factor, or a combination of any two or more thereof. Additional illustrative polypeptides that can be introduced into cells using the invention method include blood coagulation factors and lymphokines, such as tumor necrosis factor, interleukins 1, 2 and 3, lymphotoxin, macrophage activating factor, migration inhibition factor, colony stimulating factor, α-interferon, β-interferon, γ-interferon (and subtypes thereof), and the like.

As used herein, the "nucleic acid," "nucleic acid molecule," "polynucleotide", or "oligonucleotide" of the present invention includes DNA, cDNA, and RNA sequences of all types. For example, the polynucleotides can be double stranded DNA, single-stranded DNA, complexed DNA, encapsulated DNA, genomic DNA, naked RNA, encapsulated RNA, a DNA-RNA hybrid, a nucleotide polymer, and combinations thereof. Such agents may be introduced into the cell for any purpose. For example, the agents may be used in an amount to modulate cell proliferation or to elicit an immune response, either against the nucleic acid or a protein product encoded by the nucleic acid.

The polynucleotides of the present invention can also be DNA constructs, such as expression vectors. Such expression vectors may encode a desired gene product (e.g., a gene product homologous or heterologous to the subject into which it is to be introduced). A therapeutic polypeptide (one encoding a therapeutic gene product) may be operably linked with a regulatory sequence such that the cells of the subject are transfected with the therapeutic polypeptide, which is expressed in cells into which it is introduced according to one aspect of the invention methods. The polynucleotide may further encode a selectable marker polypeptide, such as is known in the art, useful in detecting transformation of cells with agents according to the invention method.

In various embodiments of the invention method, the agent can be a "proliferation-modulating agent," which alters the proliferative abilities of cells. Proliferation modulating agents include, but are not limited to, cytotoxic agents, agents toxic or becoming toxic in the presence of a protein, and chemotherapeutic agents. The term "cytotoxic agent" refers to a protein, peptide or other molecule having the ability to inhibit, kill, or lyse a particular cell. Cytotoxic agents include proteins such as ricin, abrin, diphtheria toxin, saporin, or the like.

In another embodiment, the present invention can be used to facilitate the enhanced delivery of drugs to tumors and/or other tissues. In this regard, drugs contemplated for use in the method of the invention include antibiotics such as are known in the art and chemotherapeutic agents having an antitumor or cytotoxic effect. Such drugs or agents include bleomycin, daunomycin, 5-FU, cytosine arabinoside, colchicine, cytochalasin B, daunorubicin, neocarzinostatin, suramin, doxorubicin, carboplatin, taxol, mitomycin C, vincristine, vinblastine, methotrexate, and cisplatin. Other drugs and chemotherapeutic agents will be known to those of skill in the art (see for example The Merck Index). Such agents can be "exogenous" agents, which are not normally found in the subject (e.g., chemical compounds) or can also be "endogenous" agents, which are native to the subject, including suitable naturally occurring agents, such as biological response modifiers (i.e., cytokines, hormones). Additional chemotherapeutic agents include cytotoxic agents derived from microorganism or plant sources.

In addition, "membrane-acting" agents can also be introduced into cells according to the invention method. Membrane acting agents are a subset of chemotherapeutic agents that act primarily by damaging the cell membrane, such as N-alkylmelamide, and para-chloro mercury benzoate. Alternatively, the composition can include a deoxyribonucleotide analog, such as azidodeoxythymidine, dideoxyinosine, dideoxycytosine, gancyclovir, acyclovir, vidarabine, ribavirin, or any chemotherapeutic known to those of average skill in the art.

Furthermore, in another embodiment, the methods and apparatus of the present invention can be used to administer and enhance the efficacy of vaccines. Therefore, in an embodiment of the present invention, the agent can be a vaccine. Such a vaccine may consist of inactivated pathogens, recombinant or natural subunits, and live attenuated or live recombinant microorganisms. This vaccine may also include a polynucleotide or a protein component.

DNA immunization, a method to induce protective immune responses using "naked" DNA, complexed DNA, or encapsulated DNA, is shown in U.S. Pat. No. 5,589,466. DNA immunization entails the direct, in vivo administration of vector-based DNA or non-vector DNA that encodes the production of defined microbial or cellular antigens, for example, and cytokines (e.g., IL and IFN), for example. The de novo production of these antigens in the host's own cells results in the elicitation of antibody and cellular immune responses that provide protection against challenge and persist for extended periods in the absence of further immunizations. The unique advantage of this technology is its ability to mimic the effects of live attenuated vaccines without the safety and stability concerns associated with the parenteral administration of live infectious agents. Because of these advantages, considerable research efforts have focused on refining in vivo delivery systems for naked DNA that result in, for example, maximal antigen production and resultant immune responses. Such systems also include liposomes and other encapsulated means for delivery of DNA.

Therefore, according to the present invention, a DNA or RNA molecule may be introduced as a vaccine to induce a protective immune response. In addition to encoding the gene product (i.e., active agent) to be expressed, the molecule may also contain initiation and termination signals that are operably linked to regulatory elements including a promoter and polyadenylation signal capable of directing expression in the cells of the vaccinated subject. The vaccine polynucleotide can optionally be included in a pharmaceutically acceptable carrier as described herein.

As used herein, the term "gene product" refers to a protein or peptide resulting from expression of a polynucleotide within the treated cell. The gene product can be, for example, an immunogenic protein or peptide that shares at least an epitope with a protein from the pathogen or undesirable cell-type, such as a cancer cell or cells involved in autoimmune disease against which immunization is required. Such proteins and peptides are antigens and share epitopes with either pathogen-associated proteins, proteins associated with hyperproliferating cells, or proteins associated with autoimmune disorders, depending upon the type of genetic vaccine employed. The immune response directed against the antigenic epitope will protect the subject against the specific infection or disease with which the antigenic epitope is associated. For example, a polynucleotide that encodes a pathogen-associated gene product can be used to elicit an immune response that will protect the subject from infection by the pathogen.

Likewise, a polynucleotide that encodes a gene product containing an antigenic epitope associated with a hyperproliferative disease such as, for example, a tumor-associated protein, can be used to elicit an immune response directed at hyperproliferating cells. A polynucleotide that encodes a gene product that is associated with T cell receptors or antibodies involved in autoimmune diseases can be used to elicit an immune response that will combat the autoimmune disease by eliminating cells in which the natural form of target protein is being produced. Antigenic gene products introduced into cells as active agents according to the present invention may be either pathogen-associated proteins, proteins associated with hyperproliferating cells, proteins associated with auto-immune disorders or any other protein or peptide known to those of average skill in the art.

Therefore, in one form of the invention, a desired vaccine is first introduced into a cell using known techniques. For example, the vaccine can first be introduced into the cell and then exposed to one or more nsPEF pulses in order to facilitate entry of the vaccine molecules into the nucleus, thereby stimulating secretion of the antigen produced by the vaccine molecule.

In addition, it may be desirable to introduce into cells of a subject a polynucleotide that modulates the expression of a gene, such as an endogenous gene, in cells. The term "modulate" envisions the suppression or augmentation of expression of a gene. Where a cell proliferative disorder is associated with the expression of a gene, nucleic acid sequences that interfere with the gene's expression at the translational level can be used to modulate gene expression. This approach introduces into the cells of a subject active agents capable of interfering with expression, such as antisense nucleic acid sequences, ribozymes, or triplex agents to block transcription or translation of a specific mRNA, either by masking that mRNA with an antisense nucleic acid or triplex agent, or by cleaving it with a ribozyme.

Antisense nucleic acid sequences are DNA or RNA molecules that are complementary to at least a portion of a specific mRNA molecule. In the cell, the antisense nucleic acid hybridizes to the corresponding mRNA, forming a double-stranded molecule. The antisense nucleic acid interferes with the translation of the mRNA, since the cell will not translate a mRNA that is double-stranded. Antisense oligomers of about 15 nucleotides are preferred, since they are easily synthesized and are less likely than larger molecules to cause problems when introduced into the target cell. The use of antisense methods to inhibit the in vitro translation of genes is well known in the art.

Use of a short oligonucleotide sequence (i.e., "triplex agent") to stall transcription is known as the triplex strategy, since the oligomer winds around double-helical DNA, forming a three-strand helix. Therefore, such triplex agents can be designed to recognize a unique site on a chosen gene (Maher, et al., Antisense Res. and Dev., 1(3):227, 1991; Helene, C., Anticancer Drug Design, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated. There are two basic types of ribozymes namely, tetrahymena-type (Hasselhoff, Nature, 334:585, 1988) and "hammerhead"-type. Tetrahymena-type ribozymes recognize sequences that are four bases in length, while "hammerhead"-type ribozymes recognize base sequences that are 11-18 bases in length. The longer the recognition sequence, the greater the likelihood that the sequence will occur exclusively in the target mRNA species. Consequently, it is preferred to employ hammerhead-type ribozymes over tetrahymena-type ribozymes for inactivating a specific mRNA species, and 18-based recognition sequences are preferable to shorter recognition sequences as active agents in one aspect of the invention.

The agent introduced according to the invention methods can also be a therapeutic peptide or polypeptide. For example, immunomodulatory agents and other biological response modifiers can be administered for incorporation by cells. The term "biological response modifiers" is meant to encompass substances which are involved in modifying the immune response. Examples of immune response modifiers include such compounds as lymphokines. Lymphokines include tumor necrosis factor, interleukins 1, 2, and 3, lymphotoxin, macrophage activating factor, migration inhibition factor, colony stimulating factor, alpha-interferon, beta-interferon, and gamma-interferon, their subtypes and the like.

Also included are polynucleotides which encode metabolic enzymes and proteins, including antiangiogenesis compounds, e.g., Factor VIII or Factor IX. The agent of the invention can also be an antibody. The term "antibody" as used herein is meant to include intact molecules as well as fragments thereof, such as Fab and $F(ab')_2$.

The present invention also provides gene therapy for the treatment of cell proliferative or immunologic disorders mediated by a particular gene or absence thereof. Such therapy would achieve its therapeutic effect by introduction of a specific sense or antisense polynucleotide into cells having the disorder. Introduction of polynucleotides into a cell can be achieved using a recombinant expression vector such as a chimeric virus, or the polynucleotide can be delivered as "naked" DNA for example. "Introducing" the polynucleotides into a cell encompasses any method of inserting an exogenous nucleic acid molecule into a cell and includes, but is not limited to, transduction, transfection, microinjection, and viral infection of the targeted cells.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated.

In another aspect of the present invention, the polynucleotides can be introduced into the cell by calcium phosphate and dextran co-precipitation, incorporation of the polynucleotides into lipid vesicles for fusion with the plasma membrane, and electropermeabilization or electroporation using pulsed electric fields to form "pores" in the plasma membrane. Ideally, the choice of a gene delivery system will be made by those of skill in the art, keeping in mind the objectives of efficient gene transfer, with an appropriate level of gene expression, in a cell-specific manner, and without any adverse effects.

The agent introduced into a cell can also include a detectable marker, such as a radioactive label or a fluorescent marker. Alternatively, the composition can include a photoactive modification, such as Psoralin C2. Further, the composition can include a phosphoramidate linkage, such as butylamidate, piperazidate, and morpholidate. Alternatively, the composition can include a phosphothioate linkage or ribonucleic acid. These linkages decrease the susceptibility of oligonucleotides and polynucleotides to degradation in vivo.

In another aspect, the agent of the present invention may be a pharmaceutical agent or pharmaceutically active agent. The term "pharmaceutical agent" or "pharmaceutically active agent" as used herein encompasses any substance that will produce a therapeutically beneficial pharmacological response when administered to a subject, including both humans and animals. More than one pharmaceutically active substance may be included, if desired, in a pharmaceutical composition used in the method of the present invention.

The pharmaceutically active agent can be employed in various forms, such as molecular complexes or pharmaceutically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quaternary ammonium) and the like. Furthermore, derivatives of the active substances such as esters, amides, and ethers which have desirable retention and release characteristics but which are readily hydrolyzed in vivo by physiological pH or enzymes can also be employed.

As used herein, the term "therapeutically effective amount" or "effective amount" means that the amount of the biologically active or pharmaceutically active substance is of sufficient quantity and activity to induce a desired pharmacological effect. The amount of substance can vary greatly according to the effectiveness of a particular active substance, the age, weight, and response of the individual subject as well as the nature and severity of the subject's condition or symptoms. Accordingly, there is no upper or lower critical limitation upon the amount of the active agent introduced into the cells of the subject, but should not be so large as to cause excessive adverse side effects to the cell or tissue containing such cell, such as cytotoxicity, or tissue damage. The amount required for transformation of cells will vary from cell type to cell type and from tissue to tissue and can readily be determined by those of ordinary skill in the art using the teachings herein. The required quantity to be employed in the practice of the invention methods can readily be determined by those skilled in the art.

In one embodiment of the invention method, the amount of active agent such as a nucleic acid sequence encoding a gene product introduced into the cells is a "transforming amount." A transforming amount is an amount of the active agent effective to modify a cell function, such as mitosis or gene expression, or to cause at least some expression of a gene product encoded by the nucleic acid sequence. In other embodiments, the agent may be present in an "immunogenic" amount, an "immuno-modulating" amount, or a "therapeutic amount." An immunogenic amount is an amount of the active agent effective to elicit an immune response. An immuno-modulating amount is an amount of the active agent effective to alter the immune response in some way. A therapeutic amount is an amount of the active agent effective to induce a desired immunological or biological response in order to treat a particular disorder for example.

Introduction of active agents across the natural barrier layer of skin can be enhanced by encapsulating the active agent in a controlled release vehicle or mixed with a lipid. As used herein with respect to preparations or formulations of active agents, the term "controlled release" means that the preparation or formulation requires at least an hour to release a major portion of the active substance into the surrounding medium, for example, about 1-24 hours, or even longer.

Preferred controlled release vehicles that are suitable for electrotransport are colloidal dispersion systems, which include macromolecular complexes, nanocapsules, microcapsules, microspheres, beads, and lipid-based systems, including oil-in-water emulsions, micelles, mixed micelles, liposomes, and the like. For example, in one embodiment, the controlled release vehicle used to contain the active agent for microinjection is a biodegradable microsphere. Microspheres, wherein a pharmaceutically active agent is encapsulated by a coating of coacervates, is called a "microcapsule."

Liposomes, which may typically bear a cationic charge, are artificial membrane vesicles useful as delivery vehicles in vitro and in vivo. It has been shown that large unilamellar vesicles (LUV), which range in size from about 0.2 to 4.0 μm, can encapsulate a substantial percentage of an aqueous buffer containing large macromolecules, such as DNA.

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations, making them suitable vehicles for encapsulating an active agent intended to undergo electrotransport according to the invention methods.

Examples of lipids useful in liposome production include phosphatidyl compounds, such as phosphatidylglycerol, phosphatidylcholine, phosphatidylserine, phosphatidylethanolamine, sphingolipids, cerebrosides, gangliosides, and the like. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoyl-phos-phatidylcholine.

Preparations suitable for electrotransport may include the agent with a "pharmaceutically acceptable carrier." Such carriers are known in the art and include sterile aqueous or non-aqueous solutions, suspensions and emulsions. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, fixed oils, and the like. Vehicles suitable for intercellular or intracellular injection may also include fluid and nutrient replenishers, electrolyte replenishers, such as those based on Ringer's dextrose, for example. Preservatives and other additives may also be present. For example, antimicrobials, antioxidants, chelating agents, and inert gases may also be used.

It will be appreciated by those of skill in the art that the agent can be introduced into any desired cell or cell type, including eukaryotic and prokaryotic cells. Non-limiting examples include fat cells, bone cells, vascular cells, muscle cells, cartilage cells, adult, fetal and embryonic stem cells, hematopoeitic cells, lung cells, airway cells, liver cells, intestinal cells, skin cells, nerve cells, and bacteria cells. The methods can also be used to introduce an agent into cancer cells, including cancers such as carcinomas, including adenocarcinomas, squamous carcinomas, carcinoma of the organs including breast, bladder, colon, head, neck, prostate, etc.; sarcomas including chondrosarcoma, melanosarcoma, etc.; and leukemia and lymphomas including acute lymphomatic leukemia, acute myelogenous leukemia, non-Hodgkin's lymphoma, Burkitt's lymphoma, B-cell lymphomas, T-cell lymphomas, etc. The methods can also be used to introduce an agent into cells in order to treat autoimmune disorders, cystic fibrosis, inherited disorders of host defense, inherited disorders of carbohydrate metabolism, and inherited disorders of lipid metabolism.

In one embodiment, the present invention is directed to a method of enhancing gene expression in a cell using nsPEFs. "Gene expression" as used herein is defined as the process by which the information encoded in a gene is converted into protein, peptide, or some form of RNA. In one form of the invention, cells are placed in the presence of polynucleotides being introduced into the cells. The polynucleotide is in a form suitable for introduction into the cell, such as plasmid DNA. The cells and polynucleotides are exposed to relatively long pulses in the millisecond range. These long pulses cause the outer membranes of the cells to open, thereby facilitating the transfer of the polynucleotides into the cell cytoplasm. The cells are then exposed to nsPEF pulses to facilitate transfer of the polynucleotides into the nucleus. For the long pulses, field amplitudes are low, on the order of hundreds/low thousands of V/cm. According to the present invention, these long pulses can range in duration from 0.001 to 30 milliseconds, preferably 0.1 to 20 milliseconds. The field amplitudes for the long pulses can range from 0.1 to 5 kV/cm, preferably 0.1 to 1 kV/cm. During the application of the long pulses, the free polynucleotides bind reversibly to the plasma membrane and begin their reversible insertion into the electropermeabilized membranes. The polynucleotides are translocated into the cell not only during pulsation, but also for a considerable time afterwards (Karl H. Schoenbach, Sunao Katsuki, Robert H. Stark, Stephen Beebe, and Stephen Buescher, "Bioelectrics—New Applications for Pulsed Power Technology," IEEE Trans. Plasma Science 30, 293 (2002)). According to the present invention, the nsPEF pulses can range in duration from 1 to 1000 nanoseconds, preferably 1 to 300 nanoseconds. The field amplitudes for the nsPEF pulses can range from 1 to 1000 kV/cm, preferably 10 to 350 kV/cm. The application of the nsPEF pulses results in enhanced gene expression.

In order for gene expression to occur, the genes need to enter the nucleus. For long pulses, this process seems to be determined by diffusion through the nuclear membrane. Therefore, any increase in the pore size of the nuclear membrane causes an increase in the transfer rate for genes into the nucleus. If these pulses are applied after electropermeabilization of the plasma membrane, and the genes are allowed sufficient time to diffuse into the nucleus, nsPEF pulses allow an increased flux of genes into the nucleus by opening the nuclear membrane. Alternatively, it is possible that the nsPEFs could promote the expression of genes through other undefined mechanisms such as enhanced transcription efficiency and/or enhanced transcription of RNA, and/or enhanced translation of protein by mechanisms related or not to calcium mobilization. Regardless of the mechanism, initial studies that used electropermeabilization to open the outer plasma membrane, followed by nsPEFs, resulted in increased expression of a green fluorescent protein ("GFP") reporter gene in HL-60 cells. The methods and results of these experiments are described below.

In another embodiment, the nsPEF pulses alone can be used to enhance gene expression. Because nsPEFs may lead to enhanced transcription efficiency, and/or enhanced RNA transcription, and/or enhanced protein translation, nsPEFs alone may be applied to a cell in order to enhance gene expression in that cell. The gene or genes enhanced by the present invention may be native to the cell and need not necessarily be transfected into the cell. In another embodiment, the nsPEF pulses can be used to enhance gene expression in cells that have already been transfected with DNA using any commonly known method described above including lipid transfer, DNA precipitation with calcium phosphate or dextran, and viral vectors. Following transfection, the nsPEF pulses further facilitate the transport of DNA into the nucleus of the cells. Alternatively, nsPEFs may enhance gene expression by activating transcription and/or translation machinery.

NsPEF Pulse Generator

The application of high frequency intracellular effects had been limited due to the difficulty of generating large intracellular electric fields on a time scale that is comparable to or even less than the charging time of the surface membrane. If it is assumed that electroporation of intracellular membranes (intracellular electromanipulation, "IEM") requires potential differences across such membranes on the order of 1 V, electric fields on the order of kV/cm will be needed for poration of intracellular structures with characteristic dimensions of 1 μm. Most of the unipolar pulse generators that have been used in bioelectric experiments produce microsecond to millisecond duration pulses with a rise time too slow to generate measurable intracellular effects. However, as described in U.S. Pat. No. 6,326,177, the present inventors have developed technology for generating high voltage, short duration electrical pulses that make it possible to produce electric pulses in the nanosecond range with voltage amplitudes adequate to generate electric fields near MV/cm in suspensions of cells or within tissues (Mankowski, J., Kristiansen, M. A review of Short Pulse Generator Technology. IEEE Trans Plasma Science 28:102-108, 2000). Because of their nanosecond duration, the average energy transferred to the cells/tissues by these pulses is theoretically negligible, resulting in electrical effects without accompanying thermal effects.

Furthermore, the preferred embodiment of gene delivery described above utilizes a pulse generator that can provide both classical electroporation pulses (to open the plasma membrane) and nsPEF pulses (to open the nucleus). Therefore, in one embodiment, the present invention is directed to a pulse generator that is capable of delivering two different pulse types in succession in the same apparatus. This pulse generator may also be able to vary the pulse durations, electric fields, intervals between pulses, and order of the pulses. One pulse type has a duration in the range of a classical electroporation pulse in the microsecond or the millisecond range (1 microsecond to 20 milliseconds). Such a pulse type is defined herein as a long pulse. The second type of pulse has a duration in the nanosecond range (1 to 300 nanoseconds), and defined herein as a short pulse. The time between the long and short pulses in each set can vary between 0.1 second to several minutes or hours. Either the long or the short pulse can precede the other. The electric field intensity (kV/cm) of the long and/or the short pulse in the set can vary.

Accordingly, the apparatus of the present invention can deliver dual pulses differing by these magnitudes in a single apparatus. The optimum time between pulses will be determined by the diffusion of the agent from the outer membrane to the nucleus, and is expected to be in the ms range or longer. Determination of the diffusion time is within the capabilities of a skilled artisan. The dual-pulse generator may deliver pulses variable in amplitude and duration, as well as in time difference between delivery of the pulses, in order to optimize the system for transfer of the agent into various cells or tissues. The delivery could be, for example, a cuvette (for cells in suspension) or two or multiple metal electrodes for tissue treatment. Other methods of delivery, for example, in vivo deliver of the pulses, are also envisioned by the present invention. Another alternative method of deliver is to use one or more antennas to deliver the pulse instead of or in addition to an electrode or cuvette. One or more antennas may be used independently or in conjunction with an electrode or cuvette to deliver the pulse. The antennas can be, for example, a wide-band antenna, which are used to superimpose a plurality of asymmetrical, unipolar pulses to create a single pulse of the desired duration, for example, the ultrashort pulse.

Figure 7:
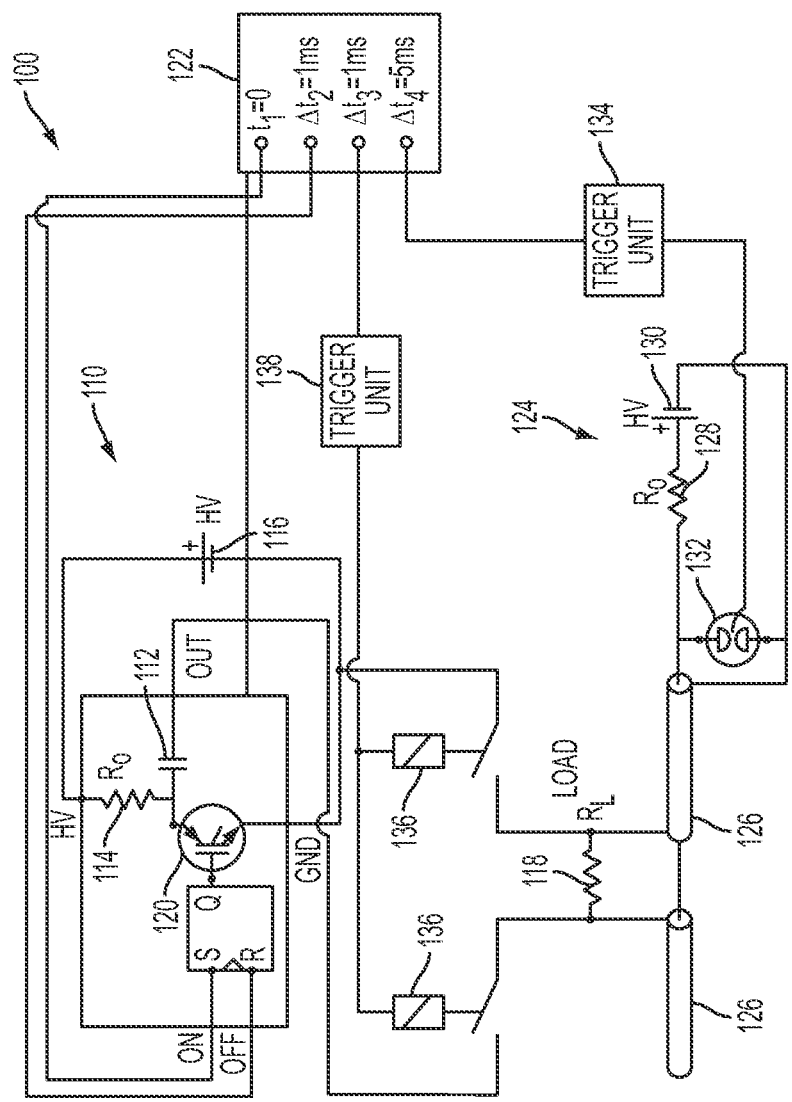
FIG. 7 is a circuit diagram for a multi-pulse generator according to one or more embodiments of the present invention.

FIG. 7 is a circuit diagram illustrating an arrangement for a pulse generator 100 according to one or more embodiments of the present invention. The pulse generator 100 of FIG. 7 is designed to delivers a set of multiple pulse types in succession within the same apparatus. According to one or more embodiments of the invention, the pulse generator 100 can be configured to deliver two different pulse types. Thus, the pulse generator 100 of such embodiments can be considered a dual-pulse generator 100. Other embodiments of the invention can allow the pulse generator 100 to deliver more than two pulse types, if and when necessary. The pulse generator 100 delivers a first pulse type having a duration in the microsecond or millisecond range, and having a low voltage, as will be discussed in greater detail below. This is considered a long pulse. For example, the first pulse type can have a duration ranging from 1 microsecond to 20 milliseconds. This range can optionally be increased or decreased by up to thirty percent (30%) depending on the specific application. The first pulse type is generally in the same range as a classical electroporation pulse. The second pulse type is considered a short pulse and has a duration that is less than the first pulse type. The second pulse also has a higher voltage than the first pulse. For example, the first pulse can have a low voltage value in the range of 0.1 to 4 kV, while the second pulse can have a higher voltage value in the range of 10 to 40 kV, although one or more embodiments of the present invention can have values ranging up to 50 kV. For example, the second pulse type can have a duration in the nanosecond range (e.g., 1 to 1000 nanoseconds). Optionally, the length of the second pulse type (or pulse) can also be increased or decreased by, for example, up to thirty percent (30%). A pause (i.e., time between the pulse types) is provided to separate the long and short pulses. According to one or more embodiments of the present invention, the pause between each set of pulses can vary between 0.1 second to several minutes or hours. Either the long or the short pulse can precede the other. Furthermore, any number of either the long or short pulses can be applied. Additionally, the electric field intensity (kV/cm) of the long and/or the short pulse in the set can vary, as necessary for various applications.

According to at least one embodiment of the present invention, the time between pulses can be determined by the diffusion of the agent from the outer membrane to the nucleus. Typically, this time interval is expected to be in the millisecond range or longer, although physical measurements of the diffusion would provide better guidance in determining the length of the pause. The dual-pulse generator 100 can deliver pulses having variable amplitude and duration. The time difference between delivery of the pulses can also be varied in order to configure the system for gene transfer into different cells or tissues. The pulses can be delivered in various ways including, for example, a cuvette for cells in suspension, two or more metal electrodes for tissue treatment, etc. Other methods of delivery such as, for example, in vivo delivery of the pulses, are also envisioned by the present invention. Another alternative method of deliver is to use one or more antennas (not shown) to deliver the pulse instead of, or in addition to, an electrode or cuvette. The antennas can be used independently or in conjunction with an electrode or cuvette to deliver the pulse. According to one or more embodiments of the present invention, the antennas can be, for example, wide-band antenna, which are used to superimpose a plurality of asymmetrical, unipolar pulses to create a single pulse of the desired duration. This type of antenna arrangement can be used to deliver a short pulse.

Referring to FIG. 7, the long pulse is generated in a first, low voltage circuit, shown in the upper left corner of the diagram and generally referenced by the numeral 110. A capacitor 112, for example with a capacitance on the order of 1 mF, is charged by a charging resistor, 114, using a high voltage power supply 116 (HV). Although FIG. 7 shows a capacitance of 1 mF, other embodiments of the invention can utilize capacitors having a capacitance ranging from 0.1 mF to 10 mF. Various other capacitance ratings can be used with the capacitor 112 depending on the specific application. The resistor 114 can have a resistance, for example, of 10 kOhms to 10 MOhms, depending on the choice of capacitor. Preferably, the resistor 114 is rated at 1 MOhms to 300 kOhms. The capacitor 112 is subsequently discharged into the load 118, which is schematically represented by its resistance ($R_L$). The load 118 could be, for example, a cuvette filled with cells in suspension, tissue between electrodes, or an apparatus that enables in vitro delivery of the pulse. The load resistance, $R_L$, is generally presumed to be on the order of Z=10 Ohms, which may range between 5 to 100 Ohms. This represents a typical value for cells in a growth medium or buffer in such commercially available cuvettes. However, the load resistance may vary according to how the biological sample to be treated is presented and the apparatus used to deliver the load.

The electrical discharge can be controlled by a transistor 120 such as, for example, an Insulated Gate Bipolar Transistor ("IGBT"), or similar component having a low forward voltage rating. Such transistors 120 are generally capable of tolerating currents for a relatively long period of time without thermal damage. Other types of transistors 120 can also be employed (e.g., MOSFETs) so long as the transistor 120 is able to handle the voltage and current being discharged from the capacitor 112. The rise and fall times of such transistors 120 can be in the range of 50 to 100 ns. The hold-off voltage of the particular transistor 120 module shown in the diagram is V=1.7 kV. For a cuvette with electrode gap of 1 cm, it is possible to generate electrical fields of E=1.7 kV/cm. The electrical field can be higher if the gap distance, d, is reduced (E=V/d). The closing and opening of the transistor 120, which acts as a switch, is centrally controlled by means of a control system 122 (or control circuit). The control circuit can be, for example, a delay generator, microcontroller, microprocessor, computer controlled circuit, etc.

The second pulse type is generated in a second, high voltage, circuit shown in the lower left corner of the diagram and generally indicated by the numeral 124. The second circuit 124 can be designed, for example, in a Blumlein configuration as shown in FIG. 7. Two transmission lines 126, or two parallel plates, can be used as an energy reservoir, similar to a capacitor. The transmission lines 126 are charged through a charging resistor 128 to a high voltage, for example, 50 kV, by means of a dc power supply 130 (HV). The resistor 128 can have a resistance, for example, of 10 MOhms to 400 MOhms. According to one or more embodiments of the present invention, the length of the transmission line 126 determines the duration of the short pulse. The duration can be calculated as the length of the transmission line 126 divided by the speed of light in the dielectric of the transmission line 126. The impedance of the transmission lines 126 can be, for example, half of the load resistance. For example, in the case of a 10-Ohm load, the impedance would be 5 Ohms. The dual-line structure of the Blumlein configuration enables full delivery of charge to the load. If, for example, only one cable were used as the transmission line 126, only half of the voltage from the power source would be applied. Thus, to deliver 50 kV across the load resistance, the transmission line 126 would need to be charged to 100 kV, which may cause technical difficulties. Using the dual-line transmission lines 126 enables maximum charge delivery to the load. Any other double line-type transmission line 126 could be used in place of the Blumlein configuration.

The second circuit 124 includes a closing switch 132 which can be, for example, a spark gap: a fast-closing switch designed to close in approximately one nanosecond, and capable of carrying high currents of I=V/Z. For example, for a voltage of 50 kV and a load resistance of 10 Ohm, the current would be 5000 A. The closing switch 132 delivers the short, high voltage pulse to the same load 118 as the first circuit 110. As previously discussed, such a load 118 can be, for example, a cuvette, tissue, etc. The closing switch 132 is controlled by a trigger unit 134, which in turn is controlled by the control circuit 122. As previously discussed, the control circuit 122 can be, for example, a delay generator, microcontroller, microprocessor, computer controlled circuit, etc. Again, any switch that is capable of withstanding the high voltages of the pulse can be used in place of the closing switch 132.

In order to prevent the high voltage pulse from damaging and/or destroying the transistor of the first circuit, at least one embodiment of the present invention provides for separation of the two circuits (110, 124) when the long pulse has been applied. This can be done using magnetic switches 136 capable of opening within a time in the range of 1-50 milliseconds, and capable of holding approximately 50 kV. This opening time is the minimum time between the long pulse and the short pulse. A trigger unit 138 is provided to actuate the magnetic switches 136. The trigger unit 138 can be controlled by, for example, the control circuit 122. According to one or more embodiments of the present invention, any switch that is reliably capable of holding a high voltage can be used (e.g., vacuum switches) in place of a magnetic switch. Furthermore, any electrical switch capable of withstanding the high voltage from the pulses can be used in place of mechanical type switches.

The system illustrated in FIG. 7 enables generation of two pulses of variable duration and amplitude. The time between the long and short pulses can also be varied. Instead of having one pulse of each kind, the pulse generator of the present invention is also capable of providing multiple pulses, both long and short pulses, etc. According to at least one embodiment of the present invention, the pulses can be controlled based on programming instructions received by the control circuit 122. Other embodiments of the invention can provide different methods of controlling pulse delivery.

The pulse generator 100 can be controlled by a sequence of instructions from the control circuit 122 shown in FIG. 7. The capacitor 112 can be initially charged to a voltage determined by its capacitance rating. The voltage can vary up to 1.7 kV through the high voltage power supply 116. At time $t_1$, the transistor 120 is triggered to close. During this time, the capacitor 112 is discharged. If the magnetic switch 136 is also closed, current will flow through the load 118 ($R_L$). The long pulse can be either exponentially decaying or a square wave, depending on the value of the capacitor 112. For example, a square wave can be used for higher capacitance values.

At time $t_2$, the long pulse is terminated by triggering the transistor 120 to stop discharge of the capacitor 112. Therefore, the time interval ($t_2$-$t_1$) determines the duration of the long pulse. The amplitude of the pulse can be controlled by various means, including through the charging circuit, the voltage source, the capacitor, and the charging resistor. At time $t_3$, the trigger unit 138 coupled to the magnetic switch 136 is actuated, thus opening the magnetic switch 136. This action decouples the first circuit 110 (low voltage) from the second circuit 124 (high voltage). At time $t_4$, trigger unit 134 actuates the closing (or spark gap) switch 132. The closing switch 132 causes the Blumlein transmission lines 126 to discharge into the load 118. It should be noted that, prior to discharge, the transmission lines 126 are charged by the power supply 130 and the charging resistor 128. This process is similar to charging the capacitor 112 of the first circuit 110, as described above. The ultra-short close time of the closing switch 132 enables delivery of the short, high voltage pulse to the load 118.

The cycle of pulse deliveries can be repeated as often as desired. Additionally, the order of pulse discharged can be altered, for example, such that the short pulse is delivered first. This alternating order of pulse delivery requires only that the magnetic switch 136 initially be in an open position. Nevertheless, as stated previously, the various embodiments of the invention can allow for any number of pulses to be delivered in any order using the pulse generator of the present invention (i.e., two short, one long; two long, one short; three short, one long; two long, two short; etc).

According to one of many applications, various embodiments of the present invention can be applied to methods of introducing an agent into a cell. The pulse generator 100 of the present invention can be used to provide fully adjustable pulsing conditions using either, or both, long and short pulse types within a pulse set. Some of these conditions include, for example, the order (i.e. short pulse first or second), duration, electric field intensity, repetition number, and/or time between pulse types within the set. One or more embodiments of the present invention allow modification of at least some of these factors (or conditions) to enhance the transfection/expression efficiency of the pulse generator 100 based on classical electroporation factors. Conditions for optimal transfection/expression efficiency differ among cell types, and can be readily determined by those of skill in the field of the invention without undue experimentation.

The foregoing detailed description includes many specific details. The inclusion of such detail is for the purpose of illustration only and should not be understood to limit the invention. In addition, features in one embodiment may be combined with features in other embodiments of the invention. Various changes may be made without departing from the scope of the invention as defined in the following claims.

As one example, the system according to the invention can include a general-purpose computer, a specially programmed (special-purpose) computer, control circuitry, controller, etc. User can interact with and provide input to the pulse generator using various systems, e.g., a personal computer or PDA, and/or remotely using various protocols to transmit date across a network such as the Internet, an intranet, wide area network (WAN), etc. Moreover, the processing can be controlled by a software program on one or more computer systems or processors, or could even be partially or wholly implemented in hardware.

User interfaces can be developed in connection with an HTML display format. Although HTML is utilized in the illustrated examples, it is possible to utilize alternative technology (e.g., XML) for displaying information, obtaining user instructions and for providing user interfaces. The system used in connection with the invention may rely on the integration of various components including, as appropriate and/or if desired, hardware and software servers, database engines, and/or other content providers. The configuration may be, preferably, network-based and uses the Internet as a primary interface with the at least one user.

The system according to one or more embodiments of the invention may store collected information and/or indexes to information in one or more databases. An appropriate database can be maintained on a standard server, for example, a small Sun™ Sparc™ or other remote location. Any presently available or future developed computer software language and/or hardware components can be employed in the various embodiments of the present invention. For example, at least some of the functionality mentioned above could be implemented using Visual Basic, C, C++, C#, or any assembly language appropriate in view of the processor being used. It could also be written in an interpretive environment such as Java and transported to multiple destinations to various users.

The many features and advantages of the invention are apparent from the detailed specification, and thus, it is intended by the appended claims to cover all such features and advantages of the invention, which fall within the true spirit and scope of the invention. Further, since numerous modifications and variations will readily occur to those skilled in the art, it is not desired to limit the invention to the exact construction illustrated and described, and accordingly, all suitable modifications and equivalence may be resorted to, falling within the scope of the invention.

Reference will now be made to specific examples illustrating the use of nsPEFs in enhancing gene expression in a cell. It is to be understood that the examples are provided to illustrate preferred embodiments and that no limitation of the scope of the invention is intended thereby.

Example 1

As stated above, experiments were performed in which electropermeabilization of cells was followed by exposure of these cells to nsPEFs. These experiments resulted in increased expression of a green fluorescent protein (GFP) reporter gene in HL-60 cells. FIGS. 1-6 show the effects of different pulses on HL-60 cells.

Materials and Methods

HL-60 cells were removed from growth media, washed, and re-suspended in low conductivity buffer (LCB) containing 0.85 mM $K_2HPO_4$, 0.3 mM $K_2HPO_4$ (pH 7.2), and 10 mM KCl (conductivity 1.5 mS/cm at 22° C.). Osmolality was adjusted to 290 mOsm by the addition of inositol. Cell suspensions ($10^6$ cells/ml) were loaded into the BioRad gene Pulser® cuvettes (Bio-Rad Laboratories, Hercules, Calif.) prior to nsPEF pulsing. A cable pulse generator was use to deliver the NsPEF pulses. NsPEFs were delivered by means of a cable pulse generator to cells suspended in a cuvette with parallel plate electrodes separated by 0.1, 0.2, or 0.4 cm. Briefly, the generator consists of 10Ω pulse-forming network (five 50Ω cables in parallel) and a spark gap in atmospheric air as a nanosecond closing switch. Post/pulse the cell suspension was removed from the pulsing cuvette and assayed.

The HL-60 cells were exposed to various pulses in the presence of 5 μg of pEGFP, a plasmid containing a nucleotide sequence coding for green fluorescent protein, downstream of the cytomegalovirus ("CMV") promoter. The following types of pulses were used: a classical plasma membrane electroporation (long) pulse administered by a BioRad Gene Pulser, a short nsPEF pulse, a combination of a long pulse followed 30 minutes later by a short nsPEF pulse, or no pulse. For instance, in the experiments depicted in FIG. 1, HL-60 cells were exposed to either a classical plasma membrane electroporation (long) pulse at 3.5 msec, 0.3 kV/cm, a nsPEF pulse at 10 nsec, 150 kV/cm, or a combination of both pulse types with nsPEF applied 30 minutes after the long pulse. Cells were then washed, resuspended in growth media, and incubated. Twenty-four hours later, 15,000 cells from the experiment were analyzed by flow cytometry for GFP fluorescence. Fluorescence was expressed as geometric mean fluorescence as indicated in the figure. The numbers next to the pulsing conditions in FIGS. 1-6 show the geometric mean GFP fluorescence observed. For instance, in the experiment depicted in FIG. 1, the control cells had a mean GFP fluorescence of 3.73, the cells exposed to the short pulse had a mean GFP fluorescence of 3.58, the cells exposed to the long pulse had a mean GFP fluorescence of 9.67, and the cells exposed to the combination of pulses had a mean GFP fluorescence of 33.58.

Results of Gene Expression Experiments

As seen in FIG. 1, the nsPEF pulse alone had no effect on GFP fluorescence while the classical electroporation pulse alone increased fluorescence by about 2.6-fold as determined by the geometric mean fluorescence. However, only about a third of the cells expressed GFP. In the presence of both pulses in succession, the GFP fluorescence was 33.58. This was about 9-fold greater than the control (3.73) and about 3.5-fold greater than that observed for the classical electroporation pulse alone (9.67). Furthermore, essentially all of the cells exposed to the combination of long and short pulses expressed GFP with greater fluorescence intensity than cells exposed to classical electroporation conditions.

FIGS. 2-6 show the results of similar experiments in which HL-60 cells were exposed to various combinations of short pulses (of varying time ranges) and long pulses (of varying voltages). Short pulses were at 60 and 150 kV/cm and ranged from 10 to 60 nanoseconds. The long pulses were in the 130 to 450 V/cm range and lasted for 3.5 milliseconds. The experiments depicted in these figures similarly demonstrated that cells exposed to the combination of the long and short pulses exhibited an increase in mean GFP fluorescence. In these experiments, the combination of pulses increased GFP fluorescence about 3.2-fold above electroporation pulses alone. For conditions that included 60 ns and 60 kV/cm as the nsPEF, GFP fluorescence increased about 3.6-fold. As with the experiment shown in FIG. 1, essentially all of the cells exposed to the combination of long and short pulses in FIGS. 2 through 6 expressed GFP with greater fluorescence intensity than cells exposed to classical electroporation conditions. These results suggest the potential to increase gene expression by combining classical electroporation pulses with nsPEF.

The many features and advantages of the invention are apparent from the detailed specification, and thus, the appended claims are intended to cover all such features and advantages which fall within the true spirit and scope of the invention. Further, since numerous modifications and variations will become readily apparent to those skilled in the art, the invention should not be limited to the exact construction and operation illustrated and described. Rather, all suitable modifications and equivalents may be considered as falling within the scope of the claimed invention.

What is claimed is:

1. A method for introducing an agent into a cell comprising:
   providing a preparation comprising the cell and an agent;
   applying a first group of electric field pulses to said preparation, wherein each pulse of the first group comprises a nanosecond pulse electric field; and
   applying a second group of electric field pulse to said preparation, wherein each pulse of the second group comprises a long pulse electric field.

2. The method of claim 1, wherein the nanosecond pulse electric field pulse is 1 nanosecond to 1000 nanoseconds.

3. The method of claim 1, wherein the nanosecond pulse electric field pulse is 1 nanosecond to 500 nanoseconds.

4. The method of claim 1, wherein the nanosecond pulse electric field pulse is 1 nanosecond to 300 nanoseconds.

5. The method of claim 1, wherein the nanosecond pulse electric field pulse is 10 nanoseconds to 60 nanoseconds.

6. The method of claim 1, wherein each pulse of the first group of electric field pulses has an electric field intensity from 1 kV/cm to 1000 kV/cm.

7. The method of claim 1, wherein each pulse of the first group of electric field pulses has an electric field intensity from 10 kV/cm to 350 kV/cm.

8. The method of claim 1, wherein each pulse of the first group of electric field pulses has an electric field intensity from 10 kV/cm to 250 kV/cm.

9. The method of claim 1, wherein the second group of electric field pulses has a duration of 0.1 millisecond to 20 milliseconds.

10. The method of claim 1, wherein the second group of electric field pulses has a duration of 0.001 millisecond to 30 milliseconds.

11. The method of claim 1, wherein each pulse of the second group of electric field pulses has an electric field strength of 0.1 kV/cm to 5 kV/cm.

12. The method of claim 1, wherein each pulse of the second group of electric field pulses has an electric field strength of 0.1 kV/cm to 1 kV/cm.

13. The method of claim 1 further comprising:
   providing a delay between the first group of electric field pulses and the second group of electric field pulses.

14. The method of claim 13, wherein the delay is zero minutes to five minutes.

15. The method of claim 13, wherein the delay is zero minutes to fifteen minutes.

16. The method of claim 1, wherein the agent is selected from the group comprising drugs, nucleic acids, protein, peptides, and polypeptides.

17. The method of claim 1, wherein the first group of electric field pulses comprises 1 to 100 pulses.

18. The method of claim 1, wherein the second group of electric field pulses comprises 1 to 100 pulses.

* * * * *